United States Patent [19]
Walters, Jr. et al.

[11] 4,354,279
[45] Oct. 19, 1982

[54] WELDING MASK CORONA BARRIER

[75] Inventors: Eugene G. Walters, Jr., Orwigsburg; Heinz E. Ruck, Media, both of Pa.

[73] Assignee: The Fiber-Metal Products Company, Concordville, Pa.

[21] Appl. No.: 112,104

[22] Filed: Jan. 14, 1980

[51] Int. Cl.³ .............................................. A61F 9/06
[52] U.S. Cl. .................................................... 2/8
[58] Field of Search ................ 2/8, 431, 432, 10; 351/44, 45

[56] References Cited
U.S. PATENT DOCUMENTS 3,112,490  12/1963  Malcom, Jr. ................................ 2/8
4,185,328  1/1980  Graveno ...................................... 2/8

Primary Examiner—Peter P. Nerbun
Attorney, Agent, or Firm—Eugene E. Renz, Jr.

[57] ABSTRACT

A corona barrier insert for a welding mask having a shield section and a main frame defining a viewing port in the shield section and a lens assembly including an outer pane made of glass and an inner pane of tinted glass to block out harmful rays. The corona barrier insert is made of a semi-rigid opaque plastic material and is of a configuration to engage in the frame defining the viewing port in a manner to block or prevent a corona or halo effect about the periphery of the lens stack.

8 Claims, 13 Drawing Figures

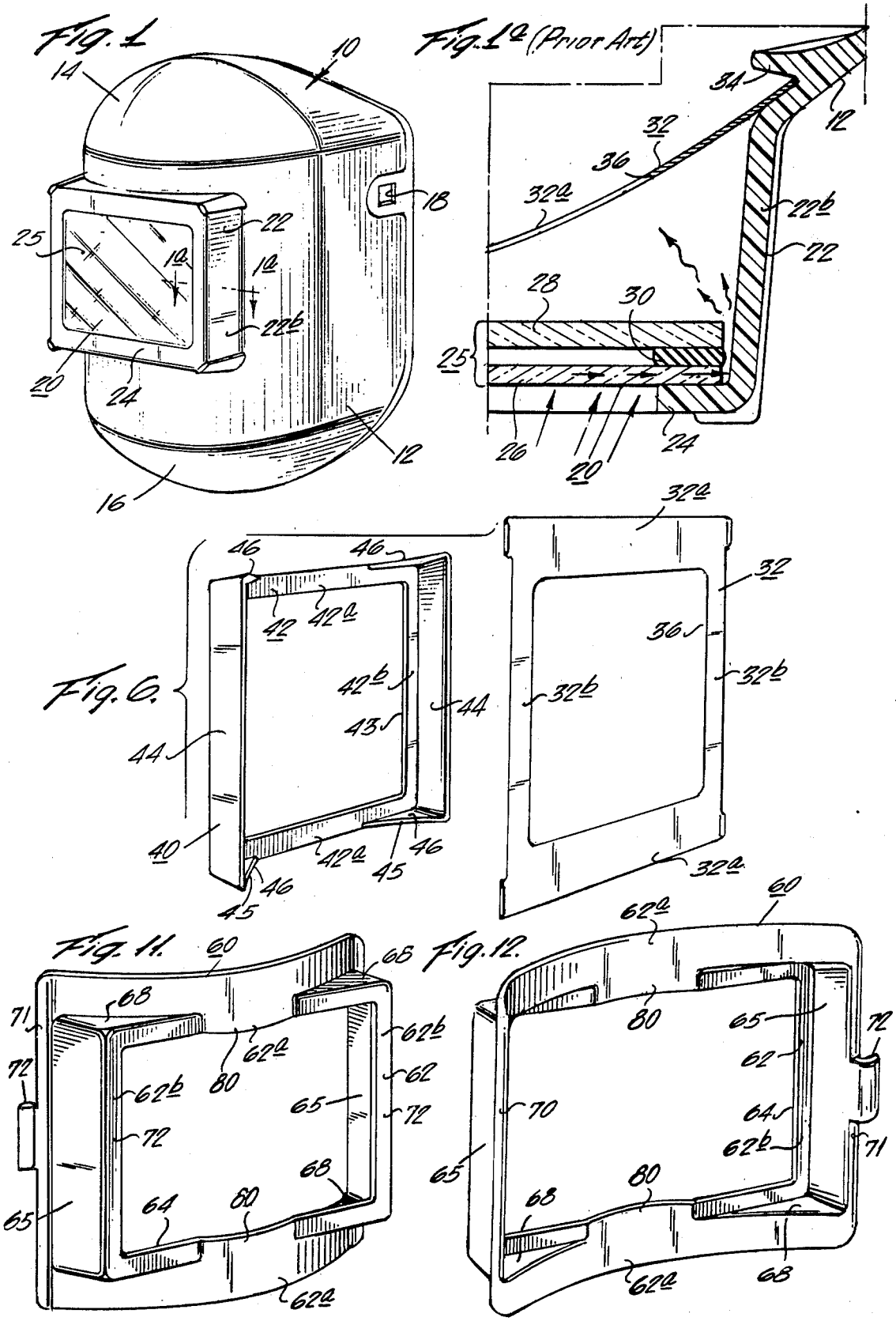

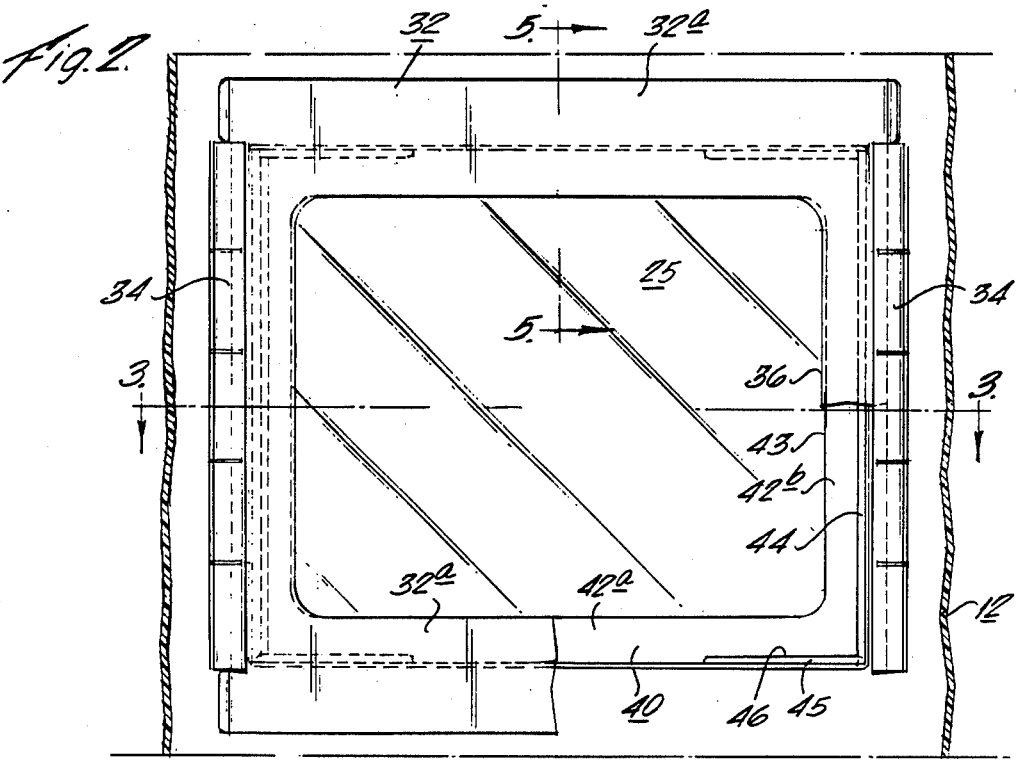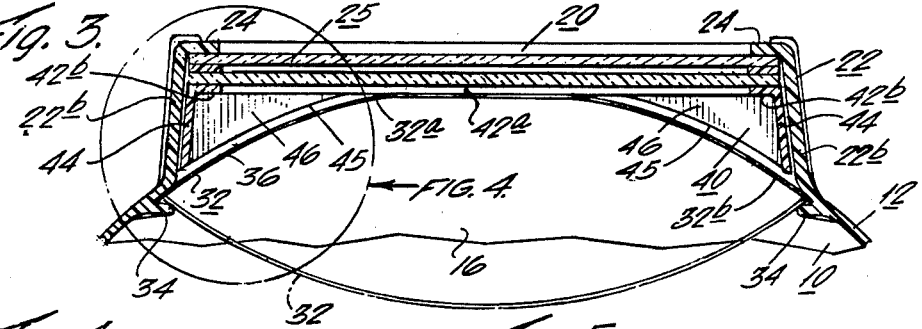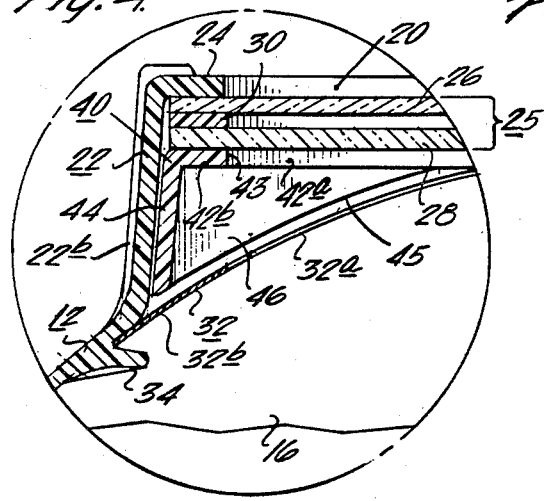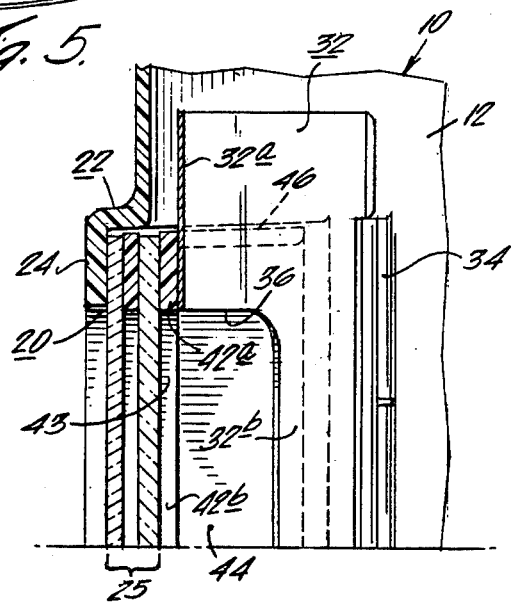

WELDING MASK CORONA BARRIER

BACKGROUND OF THE INVENTION

The present invention relates to welding masks or shields and more specifically to a novel mounting arrangement for the filter which effectively blocks the entrance of external harmful light rays to the interior of the mask to provide an effective shield against ultra-violet, visible and infrared radiation from a welding arc and thereby to protect the user against harmful radiation.

The general construction and arrangement of welding masks or shields are not new per se. Typical prior art welding masks or shields are shown in various prior United States patents including the following: R. Malcolm No. 1,904,933 issued Apr. 25, 1933; N. Anderson No. 3,257,667 issued Jan. 28, 1966; and J. N. Simpson et al No. 3,458,865 issued Aug. 5, 1969. These prior art masks are generally of similar construction and comprise a shield section preferably curved to conform somewhat to the face of the wearer which extends upwardly and rearwardly. The shield section is preferably molded as a unit from an opaque, plastic, lightweight, stiff material. The shield is normally worn on the head of the user and includes some type of head band so that it may be pivoted upwardly when not in use and easily moved to a face protecting position. When in a face protecting position, the shield is spaced forwardly of the wearer's face and extends around the side of the wearer's heaad so as to cover the head. The shield is usually provided with an enlarged rectangular opening within which is mounted a lens assembly consisting of a plurality of panes including, for example, an outer pane formed of a transparent material such as glass, an inner pane formed of similar material but which is tinted or colored so as to eliminate the transmission of harmful radiation to the eyes of the wearer which may be produced when contact is made between an energized welding rod and a work piece. The panes are usually separated by a gasket and are of a peripheral dimension conforming generally to the shape of the pocket-like viewing port in the shield but slightly undersized so that they may be easily assembled therein. The panes are usually supported in the rectangular opening by means of a spring clip. It has been found, however, that by reason of the fact that the panes do not snugly fit in the frame and the spring clip does not shield the peripheral gap between the lens stack and viewing port in the shield, there is light leakage, for example, past the filter as illustrated schematically in FIG. 1a producing a corona or halo effect which is distracting to the user and may even be harmful. Thus even where the filter plates conform with the radiant-energy transmittance requirements of the American National Standard for Occupational and Educational Eye and Face Protection, there is still the danger of light leakage past the filter which can be harmful to the user.

With the foregoing in mind, an object of the present invention is to provide a novel mounting means for the lens assembly for a shield or mask which effectively blocks penetration of harmful rays to the interior of the mask when it is in a face shielding position. This is accomplished by a mounting assembly which is of a relatively simplified construction so that the overall manufacturing costs of the entire assembly including the parts and assembling the parts together is economical and in accordance with one embodiment wherein the function of the insert and spring clip are integrated in a unitary piece is less than the cost of prior art assemblies of the type discussed above.

BRIEF DESCRIPTION OF THE DRAWINGS

These and other objects of the present invention and the various features and details of the construction thereof are hereinafter more fully set forth with reference to the accompanying drawings, wherein;

FIG. 1 is a perspective view of a welder's shield;

FIG. 1a is an enlarged fragmentary view taken on lines 1a—1a of FIG. 1 showing a typical prior art spring clip arrangement for the lens assembly and the consequent light leakage producing a corona or halo effect in the interior of the mask;

FIG. 2 is a fragmentary rear elevational view of the lens stack and mounting means for the lens in accordance with one embodiment of the present invention;

FIG. 3 is a sectional view taken on lines 33 of FIG. 2;

FIG. 4 is an enlarged fragmentary view of the section circled in FIG. 3;

FIG. 5 is an enlarged sectional view taken on lines 5—5 of FIG. 2;

FIG. 6 is an exploded perspective view of the lens mounting arrangement of the type shown in FIG. 2;

FIGS. 11 and 12 are perspective views of the combination lens retaining-light barrier bracket in accordance with the present invention.

DESCRIPTION OF THE PREFERRED EMBODIMENTS

Figure 7:
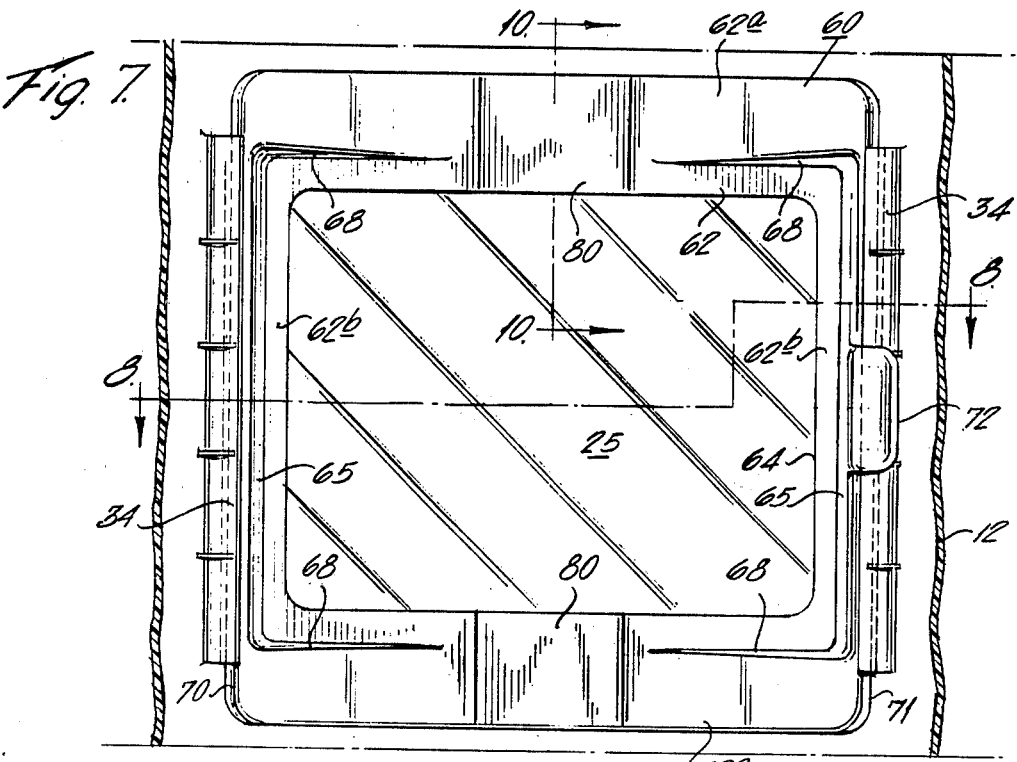
FIG. 7 is a fragmentary rear elevational view of another embodiment of a mounting bracket for a lens assembly in accordance with the present invention.
Figure 8:
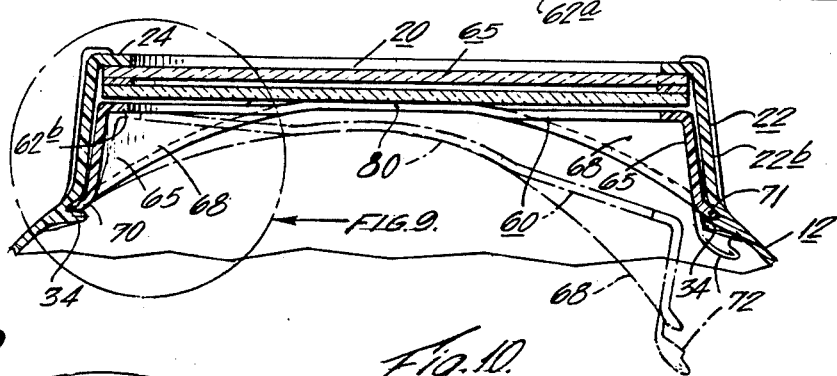
FIG. 8 is a sectional view taken on lines 8—8 of FIG. 7.

Referring now to the drawings, and particularly to FIG. 1 thereof, there is shown a typical face protecting device generally designated by the numeral 10 particularly adapted for use by welders and commonly referred to as a welding mask. The general configuration and arrangement of the welding mask are well known and include a shield section 12 preferably curved to conform to the face of the wearer, a dome-like cover section 14 extending upwardly and rearwardly from the top of the shield section and a lower section 16 extending downwardly and rearwardly from the lower edge of the shield section. These sections are generally integral and preferably molded as a unit from an opaque, plastic lightweight stiff material. The shield section 12 usually has a pair of openings 18, one on each side to permit a headband to be attached to the mask so that it can be pivoted between a face protecting position covering the face of the user including the ears and a position above the head of the user when it is not in use.

The shield section 12 is usually provided with an enlarged viewing opening or port 20 through which the user may observe his work. The opening is usually defined by a rectangular frame 22 projecting outwardly from the shield section 12 having a peripheral flange 24 defining the viewing port 20 against which a lens assembly 25 abuts. The lens unit as is typical usually comprises an outer pane 26 preferably formed of a transparent material such as glass and an inner pane 28 which may also be of a similar material but which is tinted or colored so as to eliminate the transmission of harmful light rays to the eyes of the wearer produced, for example, when contact is made between an energized welding rod and a work piece. A gasket 30 is usually mounted between the panes. The lens assembly 25 is supported against the peripheral flange 24 defining the viewing opening by means of a spring clip 32 which at its outer peripheral side edges engages locking tabs 34 on either side of the viewing opening. As illustrated the spring clip 32 is a generally rectangular open frame member having an opening 36 of slightly greater dimension than the viewing port 20. Note that the locking tabs 34 are located in the shield adjacent one end of the frame and remote from the flange 24 against which the lens assembly abuts so that when the spring clip is mounted in place only the bowed central portion of the horizontal legs 32a engage the lens assembly to support it in place.

In order to facilitate assembly of the lens unit, the peripheral dimensions of the panes are usually smaller than the dimensions of the rectangular frame 22 of the viewing or sighting port so that there is a small gap between the ends of the panes and sidewalls of the frame as illustrated in FIG. 1a. While this construction affords ease of assembly, it has been found that the light rays or photons traveling in the direction indicated by the arrows in FIG. 1a produce a corona or halo effect about the periphery of a lens assembly which is distracting to the wearer and may even be harmful. More specifically, some of the light entering the outer pane 26 is internally refracted and reflected on the sidewalls 22b of the frame to produce the corona or halo effect.

With the foregoing in mind, it is an object of the present invention to provide an improvement in assemblies of this type which effectively eliminates the corona or halo effect and yet may be assembled as easily, quickly and economically as the prior art units discussed above. To this end, in accordance with the present invention, and specifically the embodiment illustrated in FIGS. 2-6 inclusive, there is provided a corona barrier insert generally designated by the numeral 40 which seats against the lens stack and is held in place by the spring clip. The corona barrier insert 40 which is preferably made of an opaque, semi-rigid plastic material such as polypropylene, available commercially from Phillips Chemical Company under the trademark MARLEX or any other suitable material. As illustrated, the corona barrier insert 40 comprises a generally rectangular flat frame 42 with an opening 42 of approximately the same size and shape of the viewing port 20 and a pair of rearwardly projecting sidewalls running the length of the vertical legs 42b of the frame. Each of the sidewalls 44 has a pair of return corner segments 46 which extend inwardly and merge with the horizontal leg sections 42a of the frame. The corner segments are of a slightly arcuate profile or contour as at 45 which in the assembled relation complements the shape of the horizontal legs 32a of the spring clip to form therewith an effective barrier against ingress of light which may produce a corona or halo effect. (See FIGS. 2 and 3). Further as illustrated in FIG. 3, the sidewalls 44 diverge outwardly a slight degree to conform to the slightly divergent attitude of the sidewalls 22b defining the frame 22 of the sight opening or viewing port 20.

The corona barrier insert of the present invention combined with the spring clip effectively block out any light rays or photons which may travel past the lens stack creating the corona or halo effect which may be distracting or cause harmful effects on the user. The insert is easy and economical to manufacture and very simple to assemble. For example, the lens unit comprising the outer pane 26, the inner tinted pane 28 and the gasket are simply positioned in the frame 22 so that they rest on the peripheral front flange 24. Thereafter, the corona barrier insert 40 is inserted in place and the spring clip 32 bowed outwardly by the user to engage the vertical side legs 32b under the locking tabs 34. The spring clip 32 is then simply pressed inwardly so that the horizontal portions 32a of the spring clip press along a central zone Z against the back face of the horizontal leg sections 42a of the corona barrier frame and in turn exert a seating pressure against the lens stack along the zone Z. It is noted that the thickness T of the lens stack is greater than the depth D of the frame 22 adjacent with central portion thereof (see FIG. 5) so that the seating force of the spring clip operates along the central zone Z. As illustrated, the vertical side legs 32b of the spring clip 32 have tab projections 50 at the corners to straddle the locking tabs to properly align the opening 36 in the spring clip 32 with the viewing port 20 and also to ensure that the horizontal leg portions 32a straddle the juncture or top and bottom seam of the corona barrier insert and the upper and lower walls 22a of the frame of the viewing port. Note that in the assembled relation (FIG. 3) the vertical legs 32b of the spring clip are positioned closely adjacent the inner terminal edges of the sidewalls 44 of the corona barrier insert and the horizontal leg sections 32a of the spring clip 32 are closely spaced to the arcuate profile 95 of return corner segments 46 to provide an effective barrier against leakage of any light to the interior of the welding mask.

Figure 9:
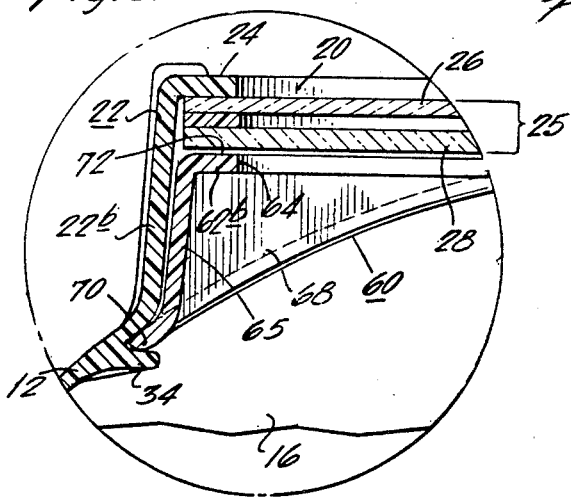
FIG. 9 is an enlarged fragmentary view of the portion circled in FIG. 8.
Figure 10:
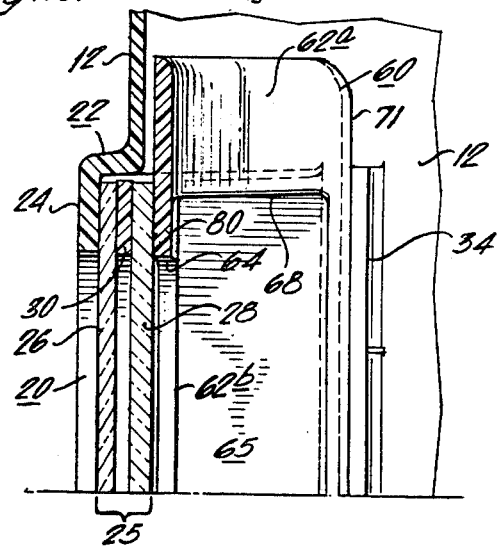
FIG. 10 is an enlarged section view taken on lines 10—10 of FIG. 7.

There is illustrated in FIGS. 7-12 inclusive another embodiment of corona barrier insert in accordance with the present invention. In this instance the unit which is generally designated by the numeral 60 is of integral one-piece construction and serves the dual function of the corona barrier insert and spring clip of the above described embodiment. This integral one-piece insert provides certain advantages over prior arrangements incorporating a spring clip. The spring clip is usually made of a pre-hardened spring steel formed in a punching operation. Fabricating pre-hardened steel is demanding on the equipment and produces relatively high maintenance and repair costs are compared to the simple plastic molding process for making the one-piece corona barrier of the present invention. Furthermore, the spring steel clips are usually characterized by sharp edges which present the risk of injury to the user. They are also difficult for the user to grasp when resting on a flat surface because of their small cross section and they are also subject to undesirable corrosion. The insert 60 may be molded of a semi-rigid opaque plastic material such as acetal, available commercially from E. I. DuPont de Nemours under the trademark DELRAN or any other suitable material. The insert 60 comprises a generally rectangular frame 62 defining a rectangular opening 64 of generally the size of the viewing port in the shield section of the mask. In this instance, however, the horizontal leg sections 62a are of bowed or arcuate cross section conforming generally to the curved shape of the shield section above and below the viewing port. The vertical side legs 62b include forwardly projecting corner sections 65 which nest in the corners of the main frame 22 defining the viewing port. The vertical side legs 62b of the frame are of a complex configuration and as illustrated in FIG. 9 are of a generally S-shaped cross section having triangular fillets 68 extending generally transversely from the horizontal leg sections. The outwardly directed edges 70, 71 of the S-shaped vertical leg sections engage behind the locking ribs 34 to seat the insert firmly in place against the lens stack. In this position, the forward faces 72 of the vertical side legs 62b are closely adjacent the inner pane and the center flexible portion presses against the stack in the manner shown in FIGS. 8 and 9 and the forwardly bowed, flexible center section 80 of the horizontal legs 62a between the corner sections 65 press firmly against the inner pane of the lens stack. Note that the lens stack is of thickness $T_1$ to project inwardly slightly beyond the arcuate trace of the shield section adjacent the center of the main frame 22 to achieve the desired pressure seating of the center sections 80 against the lens stack in this zone. Note also the sidewalls 82 of the corner sections have a slight draft or taper to parallel the slightly inclined sidewalls 22b of the main frame. This, of course, as illustrated provides a dead end path to any light which may cause a halo effect in the space between the lens stack and the sidewall of the frame 22 defining the viewing port. In the relaxed state as shown in FIGS. 11 and 12, the front face 74 of the corner sections 65 lie in a common plane and the arcuate center sections 80 of the horizontal legs 62a of the insert project forwardly of this plane so that when the insert is snapped in place, the corner sections are closely adjacent the lens pack and the flexible center sections of the horizontal legs presses firmly against the lens pack along top and bottom horizontal edges thereof as illustrated in FIG. 10. More specifically, the forwardly projecting corner sections 65 which as illustrated in FIG. 9 are closely adjacent the lens stack along the side edges thereof and inwardly from each side toward the center. In the fully assembled position shown in FIG. 8, the flexible center portions are deflected rearwardly slightly and presses firmly against the lens stack in the manner illustrated. Note also that the top and bottom frame portions or horizontal leg sections 62a are of a depth to span the gap at the top and bottom edges between the lens unit and the frame 22 in the shield section.

Assembly of the entire unit is very easy. The lens stack including the outer pane, the inner pane and gasket between the two is simply placed in the frame opening in the shield section and thereafter one side edge 70 of the insert 60 is engaged under one of the locking ribs 34. The tab 72 forming a grip portion on the opposite side edge 71 is then pressed inwardly whereby the side edge 71 snaps into or under the locking rib 34 on the opposite side of the shield section. The insert is then seated in place with the center section pressing firmly against the pane sections at the top and bottom and corner sections spaced closely adjacent the inner pane in the manner illustrated in FIGS. 8, 9 and 10.

While particular embodiments of the invention have been illustrated and described herein, it is not intended to limit the invention and changes and modifications may be made therein within the scope of the following claims.

What is claimed is:

1. A welding mask assembly comprising an arcuate shield section, a main frame projecting forwardly from the shield section having a peripheral flange with a generally rectangular opening defining a viewing port, a lens pack mounted in the main frame, a corona barrier insert made of an opaque material having a generally rectangular frame and having an opening of substantially the same size and shape as said viewing port in said main frame and including a pair of sidewalls projecting rearwardly from the front face of said insert and generally triangularly shaped corner sections adjacent said sidewalls projecting from the top and bottom edges of said front face, said insert overlying and adjacent to the peripheral gap between the lens pack and the main frame which effectively blocks external light rays which may produce a corona or halo effect interiorly of the welding mask, and a spring clip having horizontal leg portions pressing said insert against said lens pack overlying the peripheral edges of said insert and spaced closely from the inner edges of said sidewalls and said corner segments.

2. A welding mask assembly comprising a shield section, a main frame projecting forwardly from the shield section having a peripheral flange with an opening defining a viewing port, a lens assembly mounted in the main frame and slightly spaced to define a gap, said lens assembly including at least one lens, a corona barrier insert of opaque material seated against a portion of said lens assembly and overlying the peripheral gap between the lens assembly and the main frame to effectively block external light rays which may produce a corona or halo effect interiorly of the welding mask.

3. A welding mask assembly as claimed in claim 2 wherein said insert is of generally rectangular configuration including an opening of substantially the same size and shape as said viewing port in the main frame and including a pair of horizontal arcuate leg sections and vertical leg sections with corner segments projecting forwardly which recess in the main frame and are closely spaced to the lens pack, the central portion of said horizontal leg sections projecting forwardly of said corner segments.

4. A welding mask assembly as claimed in claim 3 wherein said vertical leg sections are of generally S-shaped cross section, the outer terminal edges thereof engaging vertically oriented locking tabs in the shield section on opposite sides of said viewing port.

5. A welding mask as claimed in claim 4 including a tab projecting from one of said vertical leg sections for assembly and disassembly of said insert.

6. A welding mask assembly as claimed in claim 2 wherein said corona barrier insert comprises a front face superimposed over a portion of said lens assembly and rearwardly extending sidewall portions which meet said face to overlie the peripheral gap between the lens assembly and the main frame.

7. A welding mask assembly as claimed in claim 6 wherein said corona barrier insert is of generally rectangular configuration.

8. A welding mask assembly as claimed in claim 7 wherein the sidewall portions and the front face of said insert converge to form triangular corner section, said assembly further including a spring clip overlying and conforming to said corner sections, having horizontal leg portions pressing said insert against said lens assembly, the combination cooperating to block the peripheral gap between the lens assembly and the main frame.

* * * * *